(12) United States Patent
Von Oepen et al.

(10) Patent No.: US 7,942,854 B1
(45) Date of Patent: May 17, 2011

(54) AGENT DELIVERY CATHETER INCLUDING AN ANCHOR AND INJECTION NEEDLE

(75) Inventors: Randolf Von Oepen, Los Altos, CA (US); Greg Chan, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 124 days.

(21) Appl. No.: 12/022,047

(22) Filed: Jan. 29, 2008

(51) Int. Cl.
*A61M 5/178* (2006.01)
(52) U.S. Cl. .................................. 604/164.04
(58) Field of Classification Search ............. 604/167.03, 604/164.01–170.03, 165.04, 108, 158
See application file for complete search history.

(56) References Cited

U.S. PATENT DOCUMENTS

| | | | |
|---|---|---|---|
| 5,531,780 A | | 7/1996 | Vachon |
| 6,547,787 B1 | * | 4/2003 | Altman et al. ................... 606/41 |
| 7,317,950 B2 | * | 1/2008 | Lee ............................... 607/122 |
| 2005/0070844 A1 | | 3/2005 | Chow et al. |

FOREIGN PATENT DOCUMENTS

JP 07265420 A * 10/1995

* cited by examiner

*Primary Examiner* — Nicholas D Lucchesi
*Assistant Examiner* — Diva Ranade
(74) *Attorney, Agent, or Firm* — Squire, Sanders & Dempsey (US) LLP (57) ABSTRACT

An agent delivery catheter that uses an anchoring needle and injection needle for treating tissue, such as infarcted heart tissue, includes a first needle, a second needle extendable through the first needle and a control unit for displacing and adjusting the position of both the first and second needles relative to a distal end of the delivery catheter.

16 Claims, 9 Drawing Sheets

AGENT DELIVERY CATHETER INCLUDING AN ANCHOR AND INJECTION NEEDLE

BACKGROUND OF THE INVENTION

1. Field of the Invention

This invention relates to methods and devices for treating infarcted heart tissue using a percutaneously delivered deflection catheter.

2. Description of the State of the Art

Congestive heart failure is a major disease with a high mortality rate. The disease progresses cyclically, the cause being overcompensation of the heart muscle to make up for the loss of function from infarcted myocardium. As the heart continues to overcompensate, more tissue becomes infarcted, and the heart grows in size until the anatomical valve structures can no longer operate as intended. The resulting complications become extremely serious. Existing methods for treating congestive heart failure include the removal of infarct tissue and the constraint of the heart muscle.

Another approach for treating infarct myocardial tissue is the implantation of cells, such as mesenchymal stem cells, skeletal myoblasts, bone marrow mononuclear cells, etc., which will facilitate the revitalization of the infracted heart tissue. Hereafter, these types of materials, as well as solutions containing them, will be referred to as therapeutic agents. Delivery of therapeutic agents into the infarct tissue in a minimally-invasive way generally requires that a catheter access the Internal heart chamber wall in which the infarcted area exists. This access is achieved by tracking a catheter over a guidewire that has been placed through either the vena cava or aorta, and then through the appropriate heart valve(s), to the site of the infarct. It will be appreciated, that such a beating-heart, percutaneous approach must be made while the heart muscle pulses through systole and diastole, and therefore the target site is constantly moving locations. Given that there is often a need for multiple injections using these technologies, it can be extremely difficult to place the multiple injection sites in a controlled pattern within the dynamic environment. Repositioning the device can easily result in a non-uniform, inaccurate delivery of cell boluses into the target site. There is a need to overcome the difficulty and randomness of delivery that is associated with current cell therapy devices.

SUMMARY OF THE INVENTION

The disclosure is directed to apparatus and methods for delivering a therapeutic agent into the myocardial wall intended to aid the treatment of ischemic heart tissue.

In one aspect, a device for delivering a therapeutic agent allows for a uniform distribution of therapeutic agent to the ischemic tissue, thereby improving the precision and efficacy of the overall treatment.

In another aspect, there is an injection needle design that facilitates the retention of therapeutic agent within the heart wall, thereby optimizing the cost of therapeutic agents and lowering the risk of over-dosing the diseased issue.

In one embodiment, a method includes the following steps. The catheter body is directed into the heart chamber percutaneously until the distal end is placed adjacent to the ischemic tissue. An anchor needle is extended and punctures into the heart wall. Once in place within the tissue, an injection needle is extended by advancing it through an opening or aperture of the anchor needle. The injection needle tends to take a path lateral to the access of the anchor needle and may be extended to the desired depth. Injectate is then delivered through the injection needle. The injection needle may be retracted back into the anchor needle and the anchor needle may be retrieved along with the device to complete the procedure. Injectate may be deposited at multiple injection sites by rotating the anchor needle and repeating the injection and retraction steps. This process may be repeated until a desired number of injection sites have been created.

In one embodiment, a deflection catheter for delivery of a therapeutic agent to myocardial ischemic tissue includes a first needle including a piercing tip and a shaft defining a needle axis, the shaft forming a lumen terminating at a shaft opening located at a side of the shaft, a second needle located within the shaft lumen and placed in fluid communication with the therapeutic agent, and a control unit configured to extend and withdraw the second needle from the shaft opening at an angle to the needle axis while the shaft opening is embedded within the myocardium.

The first needle may be rigid compared to the second needle, and the second needle may extend from the shaft opening at angles of between about 0-180 degrees, 60-90 degrees and 10-60 degrees. The second needle may be made from a shape memory material and preformed to have a curvilinear shape. In such case, the tip of the second needle can take a curvilinear path to the target tissue after exiting from the shaft opening.

The catheter may also include an anchor that is deployable with the first needle. The anchor helps to retain the tip of the catheter at the myocardial wall, and prevents the catheter from rotating with the first needle when the first needle is being re-positioned to deliver therapeutic agent. The anchoring member may have spikes or a curvilinear shape that resists movement or backout within the tissue.

In another embodiment, an injection needle assembly includes a first needle having a needle axis, a proximal end and distal end, and forming a lumen extending from the distal to proximal end, the lumen including an exit opening disposed transversely of the axis at the distal end, a second needle having a proximal end and a distal end and being disposed within the lumen, the distal end being disposed near the exit opening, and a control unit adapted for remotely controlling movement of the first and second needles when the injection needle assembly is integrated with a deflection catheter having a distal end and the distal end is disposed proximal to ischemic tissue.

The control unit includes a first actuator, second actuator and third actuator. The first actuator is coupled to the first needle proximal end and adapted for embedding the first needle distal end into the tissue. The second actuator is coupled to the first needle proximal end and adapted for rotating the first needle distal end after the first needle has been embedded into the tissue. The third actuator is coupled to the second needle proximal end and configured for extending the second needle distal end from the exit opening and towards a targeted portion of ischemic tissue after the first needle has been embedded into the tissue.

The first actuator may be configured to translate the first needle in one step, and then rotate the first needle in a subsequent step. The second actuator may be configured to translate the second needle while the first needle is stationary. In one case, this allows an operator to extend the first needle into the myocardium, and then extend the second needle into the tissue for treatment. After agent has been deposited, the second needle is withdrawn, the first needle rotated, and the process repeats.

In another embodiment, an apparatus for delivering therapeutic agent to ischemic tissue includes a catheter body having a proximal and distal end, a shaft selectively deployable from the catheter distal end, the shaft having a proximal and distal end, a piercing tip at the shaft distal end and forming a shaft lumen terminating at an opening formed on a side of the shaft, an injection needle having a proximal end adapted for being placed in fluid communication with the therapeutic agent and a distal end disposed within the shaft lumen, and first and second members. The first member is coupled to the shaft and configured to rotationally displace the shaft among a plurality of angles. The second member is coupled to the injection needle and configured to selectively extend and withdraw the injection needle distal end from the opening, such that after rotation of the shaft through one of the plurality of angles, the injection needle is extendable towards an ischemic tissue target. In this embodiment, the second member is configured for extending the injection needle towards a first target when the shaft opening is rotated to face a first target, and extending the injection needle towards a second target when the shaft opening is rotated to face the second target.

In another embodiment, a method for delivery of a therapeutic agent to myocardial ischemic tissue using a catheter having an anchoring needle and injection needle disposed within the anchoring needle includes the steps of percutaneously delivering the catheter to the myocardium, extending, in a first direction, the anchoring needle into the myocardium, extending, in a second direction, the injection needle through an opening of the anchoring needle and depositing the agent at a first site using the injection needle, withdrawing the injection needle into the lumen, rotating the anchoring needle, and extending, in a third direction, the injection needle through the opening and depositing the agent at a second site using the injection needle.

In another embodiment a method includes the steps of disposing the anchoring needle within the myocardium such that the exit opening faces a first tissue site, extending the injection needle from the exit opening and depositing agent at the first tissue site, retracting the injection needle into the anchoring needle, rotating the anchoring needle so that the exit opening faces a second tissue site, and extending the injection needle from the exit opening and depositing agent at the second tissue site.

Embodiments of the invention may include one or more of the following additional benefits and advantages: simplification of the procedure and reduction of the procedure time, and time spent in the heart chamber; uniform distribution of therapeutic agent within the ischemic tissue without the need to reposition the catheter, which would otherwise lead to inaccurate injections; retention of agent within the injection site, thereby reducing cost of procedure and improving the efficiency of delivery volumes; and compensation for situations where a catheter tip is not flush with the myocardium, by use of a curved or transverse path for an injection needle.

DETAILED DESCRIPTION OF THE INVENTION

Figure 1:
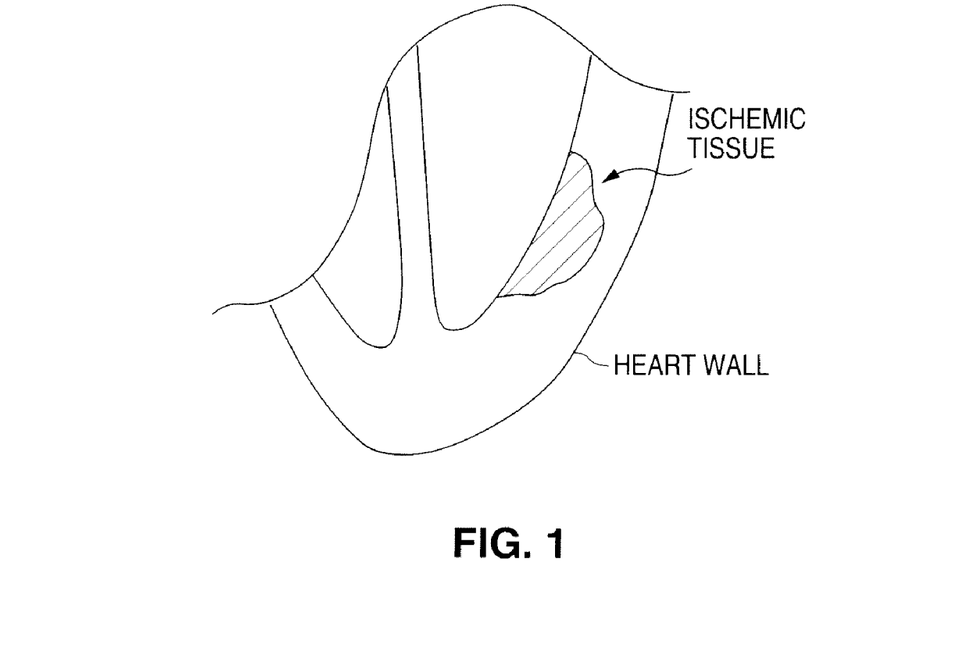
FIG. 1 is a view of a portion of the heart showing a region of ischemic tissue.

Referring now to FIG. 1, an example of an ischemic heart is shown. In this figure, the hatched portion represents the ischemic tissue, which can be revitalized by therapeutic agents. The heart chamber adjacent to the ischemic tissue is the left ventricle in this case, which would be a common disease location. However, it will be appreciated that other sites may be diseased, such as the right ventricle or atria of the heart. Further, it will be appreciated that a traditional approach to the left ventricular wall includes access into the ventricle through the aortic valve. However, this is not absolutely necessary, since access may also be gained transthoracically, transeptally, through the mitral valve, or even from crossing through a coronary vessel wall.

As will be appreciated, the invention may be practiced using a variety of deflection catheters, provided they are capable of deploying a needle in accordance with the invention and can be steered and the tip deflected so that the needle may be deployed to treat the target tissue. Preferably, the invention is practiced using one or more of the catheters disclosed in U.S. Publication No. 2005/00780844. The disclosure in this publication is herein incorporated by reference in its entirety for all purposes.

Figure 2:
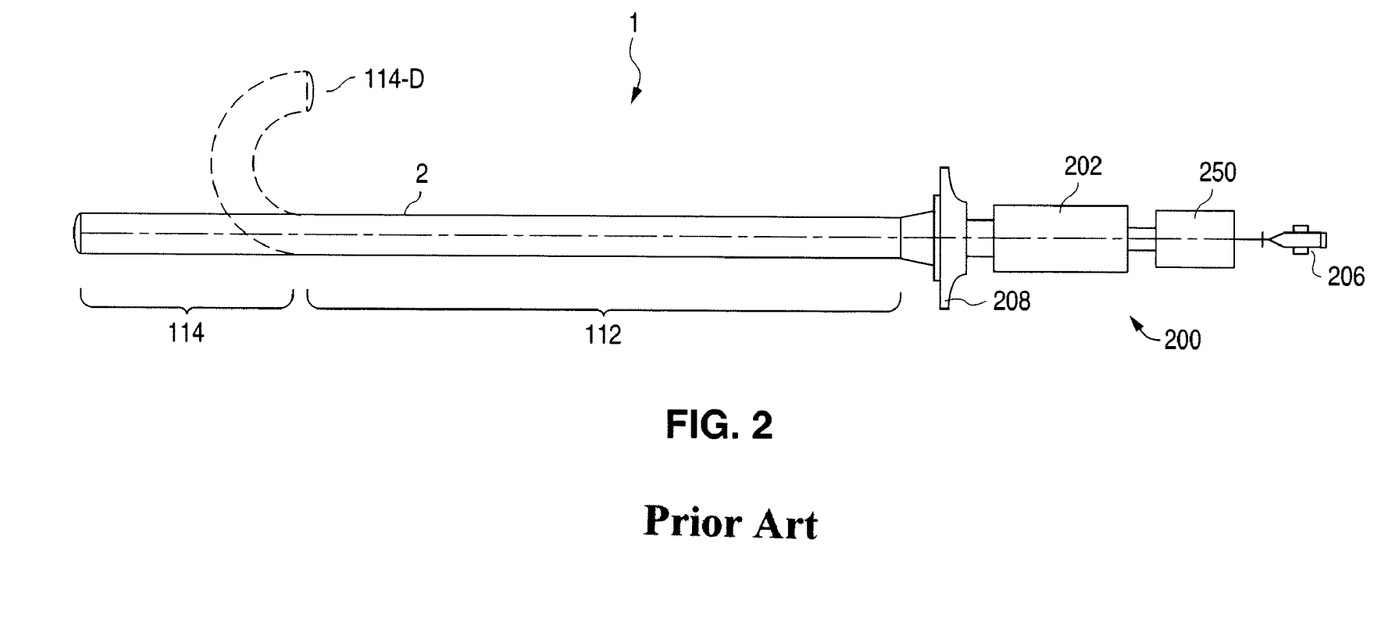
FIG. 2 is a side view of a deflection catheter.
Figure 3:
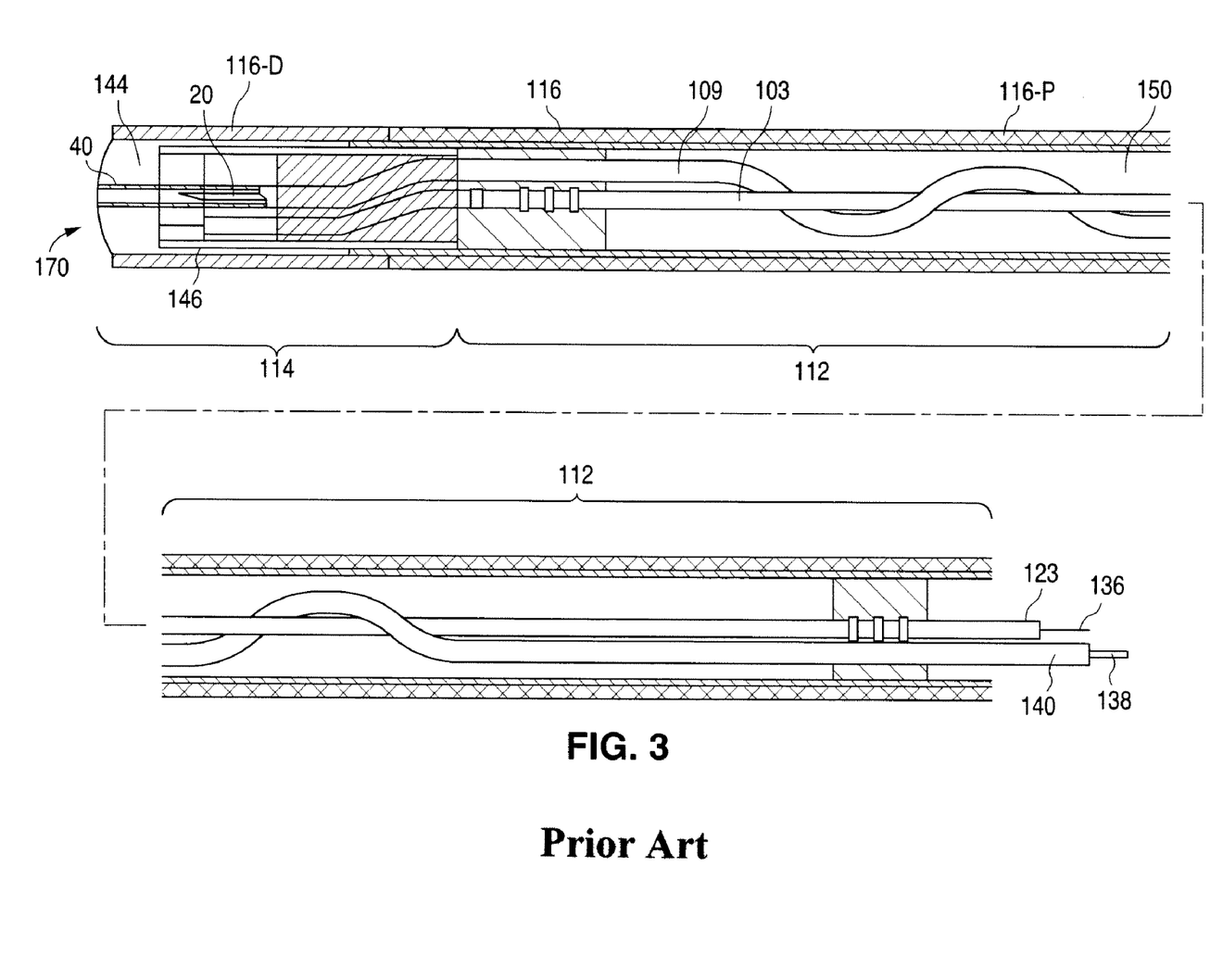
FIG. 3 is a side cross-sectional view of a portion of the catheter.

FIG. 2 illustrates one such embodiment of a deflectable catheter 1 that comprises an elongate catheter shaft 2 having a catheter proximal section 112 and a catheter distal section 114. Each section has different stiffness properties to optimize performance of the catheter shaft 2. The catheter distal section 114 is more flexible than the catheter proximal section 112. The proximal section 112 transmits torque applied to the handle 202 and distal section 114 is flexible so that it may be easily deflected laterally (114-D). The catheter 1 may be deflected at distal end 114 by pulling on at least one tendon 136 extending over the proximal and distal sections and contained with the lumen of the catheter shaft 2, as shown in FIG. 3. When deflected, the catheter distal section 114 curls up to become a deflected section 114-D.

At the proximal end, the catheter has a control portion 200 that includes a shaft 2 steering control 202 and steering guide 208, a needle control 250 and a connection port 206 for delivering therapeutic agent to a treatment site. Steering control 202 and guide 208, e.g., those described U.S. Publication No. 2005/00780844, are used to control the deflection of shaft 2 en route to, and while at the target site by pulling one or more tendons for tip deflection.

A needle 20 is disposed within the catheter shaft 101 and extendable from the end in order to deliver a therapeutic agent to diseased tissue. The needle 20 is controlled by a needle control 250 portion of the control portion 200. One or more connection ports 206 are used to place an injection needle in fluid communication with a therapeutic agent. Connection port 206 may include a pressure regulator/sensor.

As will be appreciated, the invention may be practiced by retro-fitting an existing deflection catheter with a needle 20 and needle control 250 unit, which can easily be adapted for connecting to a proximal end of a particular deflection catheter type. Accordingly, it should be understood that the invention may also be practiced by a needle 20 and needle control 250 substituted for a therapeutic tool of an existing catheter.

In a preferred embodiment, the tendon assembly 103 is located approximately in the center of the catheter shaft and the needle assembly 109 is wrapped around the tendon assembly over at least a portion of the proximal section 412 length, as depicted in FIG. 3. The number of wraps and the location of the wraps may be altered to suit a particular objective, such as to improve the usability of the catheter when it is disposed within a particular type of tortuous anatomy.

The catheter distal section 114 includes a distal catheter shaft 116-D and a compression cage 146, which is stiff axially but without any appreciable bending stiffness. The distal catheter shaft 116-D acts as an outer packaging layer for the internal components of the catheter assembly 100 that are housed in the catheter distal section 102. The compression cage provides columnar strength to the distal section 114 without increasing its bending stiffness. The catheter distal section 114 will deflect when tendon 136 is pulled using the steering mechanism 202. Proximal to distal section 114 the tendon 136 is shifted from the center of the catheter shaft 116 to off-center. By being off-center, tension in the tendon 136 will deflect distal section 114 as illustrated by 114-D. The needle assembly 109, which includes needle 20 and sheath 40, extends parallel to the tendon 103 over the distal section 114 and is disposed at the center of the shaft lumen over distal section 114. At tip 170 of the catheter there is a passageway 144a formed in the anchor 144 for passage of the needle 20 when the tip 170 is disposed at a treatment site.

Figure 5:
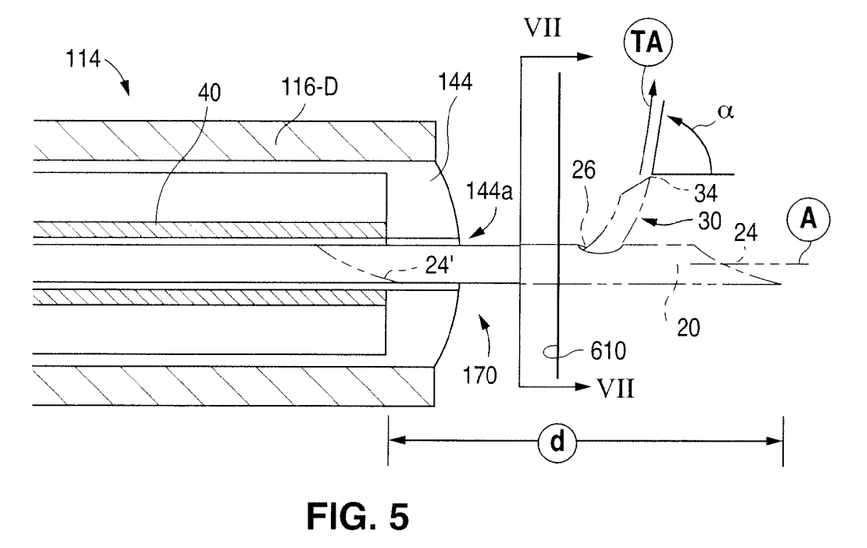
FIG. 5 is a cross-sectional view of a distal end of the catheter disposed adjacent to ischemic tissue.

Referring to FIG. 5 a cross-sectional view of the end portion of distal section 114 of the catheter 1 is shown. Anchor needle 20 has been deployed from end 170, and pierced through the myocardial wall to treat ischemic tissue (hereinafter referred to as either "ischemic tissue", "target tissue" or "tissue" unless stated otherwise). With the anchor needle 20 embedded in the tissue 610 a second, injection needle 30 is deployed from anchor needle 20 to deliver therapeutic agent to the tissue.

Figure 4:
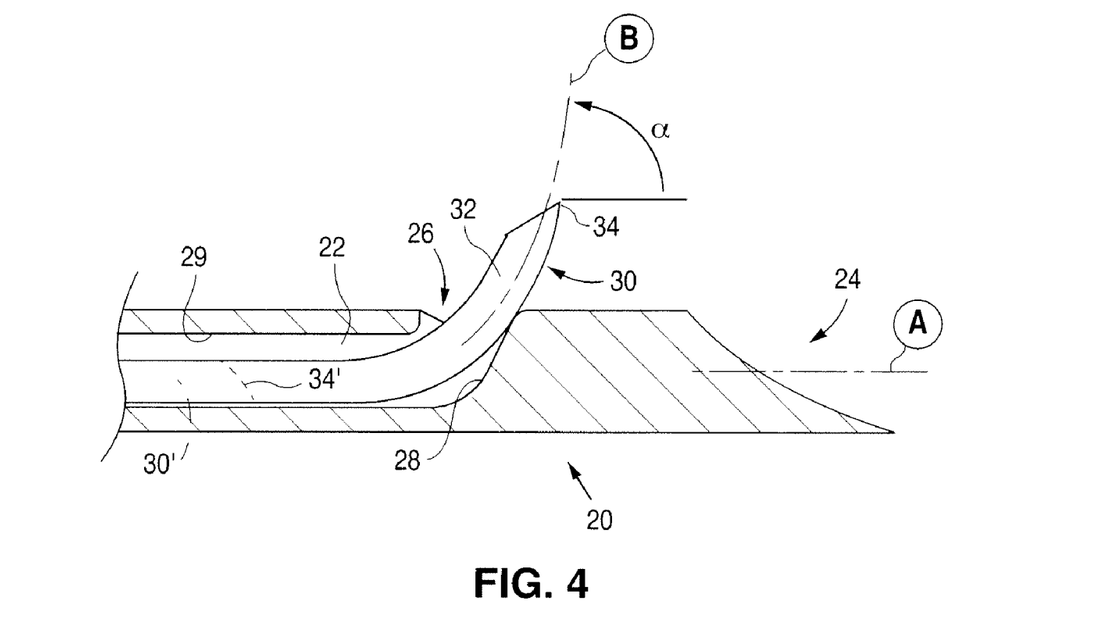
FIG. 4 is a cross-sectional view of a portion of an anchor needle of the catheter.

Referring now to FIG. 4, a close-up, cross-sectional view of the distal section of the anchor needle 20 is shown. The anchor needle 20 includes a piercing tip 24, which may take the shape of a pointed or beveled tip. The inner walls of the needle 20 form a lumen 22 that terminates inboard (leftward in FIG. 4) of tip 24, such that an opening 26 is formed traverse of the needle axis A or at the side of the needle 20. The lumen includes a straight section 29 and a sloped section 28 that terminates at opening 26. Sloped section 28 extends at an acute angle to the needle axis A, as shown, but may extend at other angles, non-parallel to the needle axis A. The needle may be formed by beginning with a tube that is then crimped at the end to form a piercing needle tip. Also, the tube could be filled at the end and then beveled by grinding or laser cutting to form the tip. In some embodiments the lumen 22 does not terminate inboard as depicted. The needle 20 may have an open end that punctures tissue by virtue of the size of the needle, or due to a beveled tip.

The lumen 22 is sized to receive the selectively deployable and retractable injection needle 30. Needle 20 may be understood as a transport for injection needle 30 to a treatment site, and a vehicle for guiding injection needle 30 to the desired target. The injection needle 30 is hollow, flexible in comparison to the needle 20, and used to deliver a therapeutic agent to the tissue 610 through its end 34. The end 34 may be a sharpened tip to facilitate easy penetration into the tissue 610. During transit to a treatment site needle 30 is disposed within the lumen 22, inboard of opening 26, as indicated by 30'. End 34 may be sharpened using grinding or cutting processes that are well known in the art for forming injection needles.

Needle 30 is preferably formed from a shape memory material such as Nitinol and preformed to take on one or more curvilinear shapes before being inserted through lumen 22. Thus, needle 30 is in a pre-stressed state when passed through the lumen 22 during assembly, and may re-take substantially the same preformed shape upon exiting from opening 26 at a treatment site. Needle 30 is preferably preformed, but it may be inserted into lumen 22 as a straight wire. In this alternative embodiment, the needle 30 exit angle and angle of the tip 34 relative to the needle 20 axis A may be constant, with the exception of slight angular variations caused by needle deflection within the tissue, etc.

The needle 30, when pushed outboard (rightward in FIG. 4) towards opening 26 and extends outside lumen 22 as shown in FIG. 4, begins to re-take its preformed shape, which can cause tip 34 to travel along pathway B. According to the extent that needle 30 is extended outward and degree of curvature over its length, needle 30 may extend transversely over a range of angles α relative to the anchor needle axis A. Angle α, which may correspond to both or either of the exit angle of needle 30 or angle of tip 34 relative to needle axis A, may range from about 10-30, 30-60, 60-90, 90-120 or greater than 120 degrees. Further, it will be understood that these angles may be selectively varied by the extent to which needle 30 is extended from opening 26.

Carrying the therapeutic agent in a second needle 30, which can be manipulated separate from anchor needle 20, has a number of advantages that will be realized by those skilled in the art in view of this disclosure. As depicted in FIG. 5, needle 30 may be shaped to extend, or simply extended from opening 26 at angle α so that therapeutic agent TA can be deposited in a direction transverse to the direction that the needle anchor 20 was inserted into the tissue. Further, needle 20 may be rotated and needle 30 re-deployed without removing the needle 20 from the tissue 610.

It will be understood that these aspects of the disclosure can improve the efficiency of therapeutic agent delivery and reduce time spent treating tissue in the heart. The disclosure provides a way to (1) increase the efficiency of a delivery volume, (2) gain better access to tissue that cannot be mated flush with the catheter tip 170, and (3) to enable needle 30 to be deployed at a plurality of target sites, over a range of angles about axis A, so as to achieve a more uniform distribution and concentration of bio-agent.

Figure 7:
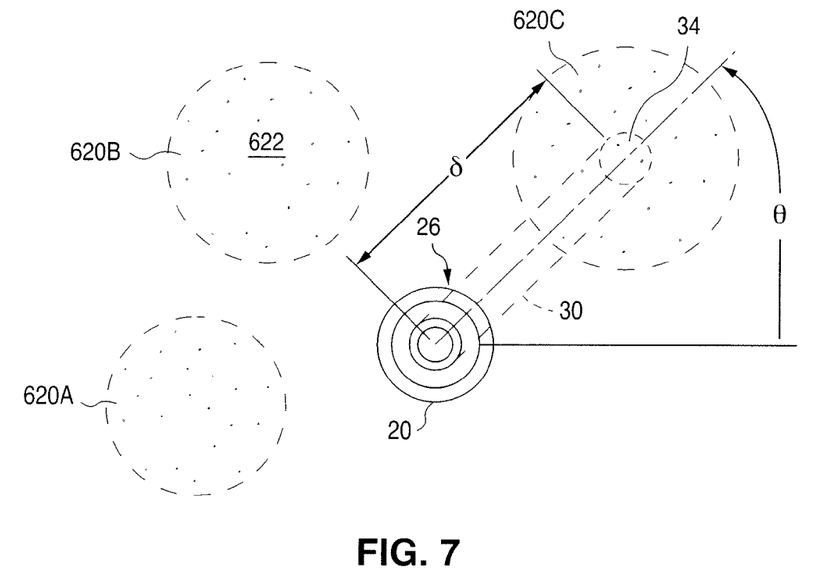
FIG. 7 is a frontal view of the needle of FIG. 4 treating ischemic tissue, as viewed from Section VII-VII in FIG. 5.

As to (1), the therapeutic agent may be denied an exit passage when the needle 20 is removed, because the agent was injected in a direction transverse to the needle 20 penetration direction. When a single needle is used to deposit a therapeutic agent, the penetration direction may be the same as the direction in which agent was deposited, or the agent exits proximal to the opening formed by the needle. In either case, the agent may leak from the tissue when the needle is removed. Because the injection pathway of needle 30 is curvilinear and sometimes distal of needle 20, and passes through cardiac muscle along different grain planes, a bio-agent may be less likely to leak from the injection site after the needle 20 is removed. As to (2), it is possible to access specific areas of tissue that may not be accessible using a single needle extended from the catheter tip 170. Needle 30 may extend from needle 20 over a variety of directions. Thus, needle 30 may be used to access difficult-to-reach tissue while needle 20 serves as an anchor. As to (3), needle 30 may be deployed over a range of angles about axis A by rotating needle 20 at the treatment site. This is depicted in FIG. 7. Both the angle θ and deflection length δ can be varied by rotating needle 20 about axis A and extending/retracting needle 30. Thus, treatment sites 620A, 620B and 620C, can be accessed while needle 20 remains embedded in the same location, thereby serving as an anchoring needle.

Needle Control

Figure 6A:
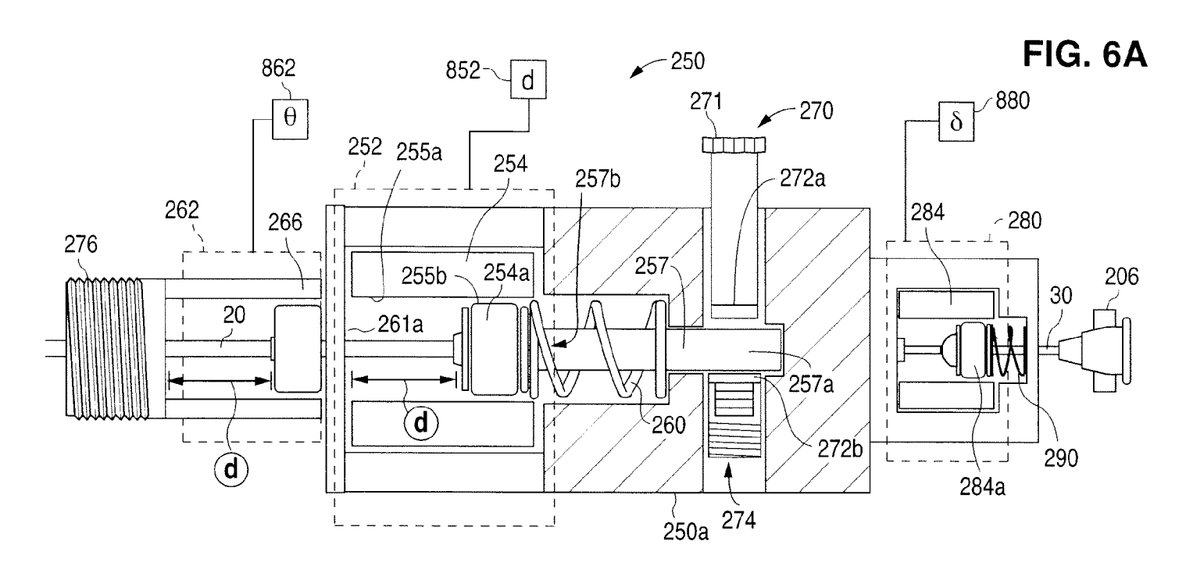
FIGS. 6A-6B are side, partial cross-sectional and top views of a needle control portion of the catheter.
Figure 6B:
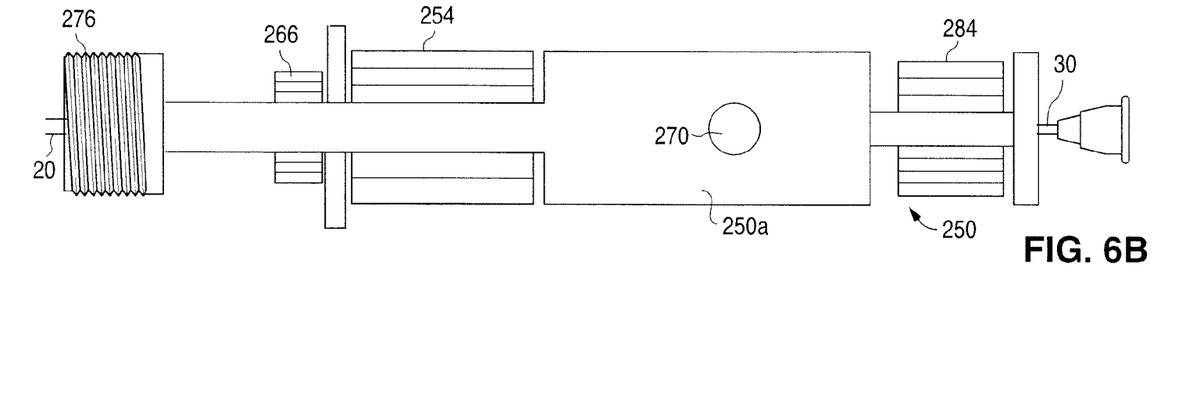

Deployment of needle anchor 20, and injection needle 30 as just described may be performed at the proximal end by a number of needle control methods. For example, needles 30 and 20 may be controlled by dials that operate worm gears for extending and retracting needles 20 and 30 independently of each other, and needle 20 may include a rotation wheel in series with its extension/retraction dial. Such a system is depicted in FIGS. 6A and 6B. FIG. 6A shows a partial schematic, cross-sectional side view of a needle control 250 and FIG. 6B depicts a top view of the needle control 250.

Needle control 250 may include the following functional components: an anchor needle rotation part 262, an anchor needle extension part 252, an anchor needle lock 270 and an injection needle extension part 280. These components of needle control 250 are integrated into a housing 250a. At a distal end thereof, housing 250a includes a connector 276 having, e.g., a rotatable connecting sleeve 276 that may be engaged via a threading with a proximal connecting end of the catheter's steering control. At the proximal end of needle control 250, there is connection port 206, which is used to place a therapeutic agent in fluid communication with the lumen of the injection needle 30.

As shown in FIG. 6A, anchor needle 20 and injection needle 30 extend through a bore of the housing. Anchor needle 20 terminates at injection needle extension part 580, as shown. In some embodiments, needle 20 terminates distal of connector 276. In these embodiments, the tube indicated as needle 20 in FIG. 6A would be a separate tube that is part of housing 250a. This tube could be releasably connected in translation and rotation to a proximal end of needle 20 by a suitable connecting sleeve. This embodiment may be desired as it can simplify assembly of needle 20 with needle control 250. Needle 30 may enter this tube at the same location shown in FIG. 6A.

Anchor needle extension part 252 is used to extend and retract anchor needle 20 from distal tip 170. When deployed, needle 20 moves towards the left in FIG. 6, and when retracted towards the right in FIG. 6. Needle 20 is manually moved left or right by turning a dial 254 coupled to needle 20 through a worm gear mechanism. This mechanism is formed by a first cylindrical piece 254a that rotates between two bushings retained on the anchor needle 20 outer surface. Piece 254a has a first threading 255b that meshes with a second threading 255a formed on the inner surface of a cylinder associated with dial 254. When dial 254 is rotated, e.g., clockwise, piece 254a rotates about needle 20 and advances to the left (anchor needle is extended out from distal tip 170). When rotated counterclockwise anchor needle 20 is moved to the right (anchor needle is pulled back into the distal tip 170). Piece 254a is spring-biased towards the left in FIG. 6 by a compression spring 260 to reduce the tendency of the worm gear to be back-driven when resistance is faced during needle 20 deployment.

A collar 257, surrounding needle 20, is connected to the rightmost bushing at 257b and extends towards the right. This collar 257 is used to restrain movement left or right for anchor needle 20, while still allowing needle 20 to rotate about its axis A via needle rotation part 266. When needle 20 has been deployed a desired distance, the needle lock part 270 is used to hold collar 257 in place. Lock 270 includes a pair of co-acting jaws 272a, 272b, operated by a knob 271. The lock 270 applies pressure through jaws 272 to surface 257a of collar 257, thereby restraining translational but not rotational motion of anchor needle 20.

The dial 254 is permitted to translate over a distance d which may correspond to the maximum deployable position of the needle anchor 20. In some embodiments, anchor needle 20 extension from tip 170 may be more closely monitored, such as by viewing a nearby display 852 that indicates the actual displacement from the tip 170 as dial 254b rotates. The displayed displacement may be provided through a position encoder coupled in rotation to the dial 254. Alternatively, if the desired displacement for needle anchor 20 is the same for all procedures, it may be pre-set into needle extension part 252, e.g., by limiting the travel of piece 254a to the distance d as shown.

Anchor needle rotation part 262 is used to rotate anchor needle 20 about axis A (FIG. 4) when anchor needle 20 is embedded in the target tissue, and may also be used to actuate the helical anchor mechanism depicted in FIGS. 9A-9D, as discussed in more detail, below. Part 262 may include a wheel 266. Wheel 266 advances left or right with anchor needle 20 as dial 254 is turned. Thus, the travel distance d provided for piece 254a may correspond to the travel distance provided for wheel 266, as indicated in FIG. 6A.

Wheel 266 is used to manually rotate needle 20 through a plurality of angular positions θ, so as to position opening 26 (at the distal end of needle 20) in the proper orientation for injection needle 30 deployment. Referring to FIG. 7, which shows needles 20 and 30 at a target tissue site, the angle θ selected using needle rotation part 262 determines the angular location 620C where therapeutic agent 622 will be deposited by injection needle 30. In this regard, wheel 266 may be configured to move or click through a predetermined range of angles when depositing agent at the treatment site. This may be preferred as it will allow an operator to more quickly deposit agent over the ischemic tissue area, thereby reducing time spent in the heart.

In some embodiments, it may be desirable to monitor the angular position θ of opening 26 (and therefore the deployment direction of injection needle 30) during treatment so that a desired placement of therapeutic agent at sites 620a, 620b and 620c can be achieved for a specific condition or site being treated. This may be done by coupling rotation of wheel 266 to a position encoder, as before, so that the angular position θ can be monitored on a nearby display 862.

Injection needle 30 extension is controlled by injection needle extension part 280 which may be essentially the same mechanism as anchor needle extension part 252. Thus, injection needle 30 may be retracted or deployed by rotating a dial 284 clockwise or counterclockwise, respectively, which causes the worm gearing to move injection needle 30 left or right in FIG. 6.

As in the case of anchor needle 20, the displacement δ of injection needle 30 may be monitored by a position encoder or potentiometer coupled to rotation of dial 284 and monitored on a nearby screen 880. Alternatively, if the desired displacement δ for injection needle 30 is the same for all procedures, it may be pre-set into needle extension part 280 by providing a predetermined maximum travel distance, as in the case of needle extension part 252.

Referring now to FIGS. 5, 6, and 7, a procedure for depositing therapeutic agent at locations 620A, 620B and 620C using needle control 250 may proceed as follows. After catheter tip 170 has been positioned at the target tissue 610, needle anchor 20 is extended a distance d by turning dial 254 of the needle extension part 254 clockwise until piece 254a abuts wall 261a. Once fully displaced, the jaws 272a, 272b are pressed down on collar 257 by turning knob 271. Anchor needle 20 is now fixed in translation and embedded at the target.

The myocardial wall is moving during the procedure. Needle anchor 20, embedded into the tissue, anchors the tip 170 of the catheter 1 at the target tissue. As discussed earlier, this anchoring of the catheter tip 170 at the target tissue allows the therapeutic substance to be deposited in the tissue with greater accuracy and, over a number of locations without removal of needle 20.

Injection needle extension part 280 is then used to deploy injection needle 30 from needle opening 26 a distance δ by rotating dial 284 clockwise (FIG. 7). Therapeutic agent is deposited at site 620C. After depositing the agent at site 620C, injection needle 30 may be extended further to deposit therapeutic agent at a different site, further out from opening 26. Next, injection needle 30 is retracted back into lumen 22 by rotating dial 284 counterclockwise. Needle 20 is then rotated to a new angular station using wheel 266, i.e., needle 20 is rotated an angle θ so that opening 26 is positioned to face tissue located at 620B in FIG. 7. Injection needle 30 is then, once again extended from opening 26 by clockwise rotation of dial 284 and therapeutic agent deposited at site 620B. This process may be repeated as many times as necessary. the end result is a more uniform distribution and concentration of agent delivered to the target tissue.

After completion of the procedure at the target site, injection needle 30 is withdrawn back into its stowed position using dial 284. Lock 270 is then released from collar 257 so that needle 20 may be retracted back into the catheter distal section 114 by counterclockwise rotation of dial 254.

Anchoring Mechanism

In some embodiments, the catheter may also include at its distal end an anchoring mechanism or other device related in function, that may be actuated when needle anchor 20 is deployed. Such a device or mechanism may be helpful to retain the catheter tip 170 position and orientation relative to the myocardium. Indeed, such a device can be helpful to both maintain the needle 20 in the target tissue while the myocardial wall moves, as well as to prevent distal section 114 from rotating as the needle 20 is rotated during a treatment process at the site. Without such a rotational restraint, distal section 114 may rotate with the needle 20, which can cause needle 20 to become dislodged from the tissue.

If the catheter 1 is passed through tortuous anatomy and/or its distal section 114 deflected a significant degree in order to locate tip 170 at the target tissue, there may be a significant amount of surface contact between the needle anchor 20 and its sheath 40 over the catheter length, which may result in an increase in resistance to rotation of the needle 20 relative to needle sheath 40. The user may then increase the applied torque at proximal end in order to cause the needle anchor 20 to rotate so that opening 26 can be positioned to face a new treatment site. If the resistance to rotation between the needle 20 and sheath 40 is sufficiently high, the applied torque may cause the distal section 114 and needle 20 to rotate as one body, thereby causing dislodgment of the needle 20 from the tissue.

When a torque applied to a body does not act solely along a principle axis of the body, the torque applied at a proximal end may induce significant lateral and axial displacement at a distal end as the body rotates in response to the applied torque. Thus, when there is a sufficiently high degree of frictional force resisting relative rotation between the needle 20 and the sheath 40 due to, e.g., the serpentine shape of the catheter at the treatment site, the torque applied at the proximal end of the needle anchor 20 (by the needle extension part 252) may cause the distal section 114 to rotate with the needle anchor 20. This may cause significant lateral and axial displacement of the distal section 114 which can dislodge the needle anchor 20 from the tissue wall. It may be desirable, therefore, to provided an anchor that restrains rotation of the catheter distal end when a torque is applied to needle 20.

In some embodiments, an anchor mechanism may be installed at the catheter distal section 114 such that its deployment is induced by needle 20 deployment, e.g., the anchor, coupled in translation to the needle 20, may be deployed with the needle 20 when dial 254 is turned clockwise. In other embodiments, the anchor mechanism may be actuated and/or adjusted at the proximal end, independently of the needle anchor 20. In other embodiments, the proximal end of the catheter 1 may include a pressure source that is capable of pulling a vacuum over the central lumen 150 such that distal tip 170 is retained at the myocardium by a pressure differential between the lumen 150 (in fluid communication with the myocardium) and outside the catheter. In this embodiment, the distal section 114 is held at the target tissue by suction.

Figure 8A:
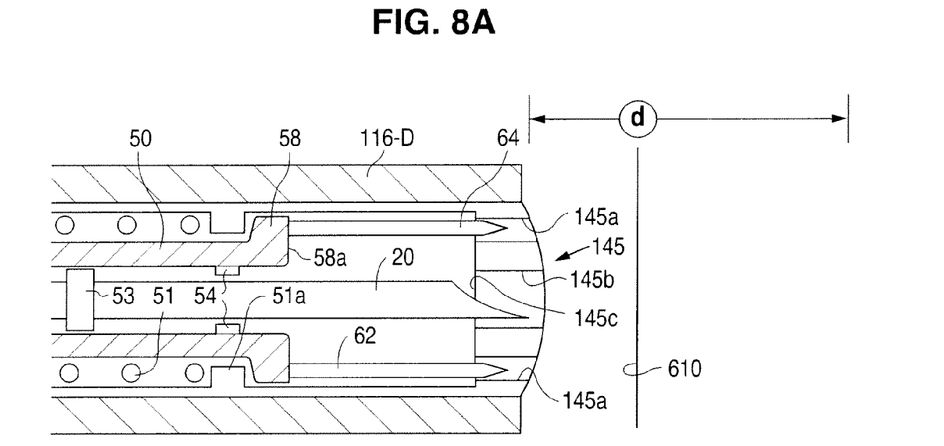
FIGS. 8A-8B are side cross-sectional views of a first embodiment of an anchor mechanism for the catheter disposed adjacent to ischemic tissue.
Figure 8B:
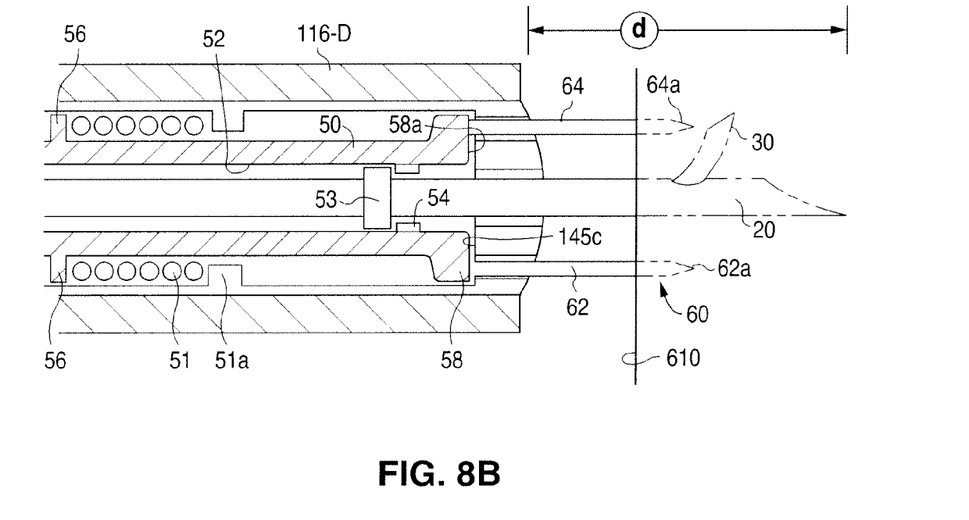

Referring to FIGS. 8A and 8B, in one embodiment, an anchoring mechanism includes one, two, three, four or more elongate, pointed or piercing spikes 60 deployable and retractable from a modified tip 145 of the catheter distal section 114. Tip 145 forms a center passage 145b for needle 20 and passages 145a for spikes 62 and 64 to extend and retract through tip 145 with needle 20. FIG. 8A depicts the position of spikes 60 and needle 20 when the catheter distal section 114 is disposed at the target tissue 610. FIG. 8B depicts the spikes 60 and needle 20 embedded into the tissue 610, with the injection needle 30 deployed to deliver a therapeutic agent to the target.

Spikes 60 penetrate the tissue 610 with the needle anchor 20 when the needle 20 is deployed. Spikes 60, being offset from the needle anchor 20, will resist rotation of the distal section 114 as the user applies a torque to the needle anchor 20 at the proximal end. The tips 62a, 64a may have a barb to assist with retaining the distal section 114 in position. In some embodiments, the spikes 60 may extend straight when extended through passages 145a as shown. In other embodiments, spikes 60 may be preformed as curved spikes so that when deployed from the tip 145 they diverge outwardly from the passages 145a.

In the illustrated embodiment, all aspects of the catheter 1, needle control 250 and method of use may be the same, except the following additional features provided by the spikes, and related mechanism(s)/structure to facilitate deployment and retraction of spikes during a procedure. Shown are two or more spikes 62 and 64 mounted to a disc 58 portion of a needle sheath extension 50. Needle 20 extends through the center of the sheath extension 50. A proximal end of extension 50 terminates within distal section 114. Although extension 50 may be regarded as a sheath extension for needle 20, it need not be connected to the sheath 40. Further, sheath 50, spikes 60 and the structure associated with deployment of spikes 60, discussed below, need not cause an unacceptable increase in the bending stiffness of distal section 114, as would be understood.

The spikes embodiment of the anchor mechanism depicted in FIGS. 8A-8B includes a spring biasing portion that will cause spikes 60 to retract when needle 20 is retracted back into the catheter following completion of the treatment at the target tissue site. Deployment of the spikes 60 is accomplished by abutting contact between a collar 53 and annular ridge 54 located at an axial station on the inner surface of sheath 50. Collar 53 and ridge 54 are located relative to each other so as to achieve a desired degree of extension of spikes 60 when needle anchor 20 is extended a distance d. The spikes 62a can be connected to disc 58.

As shown in FIG. 8B, spikes 60 are fully deployed when wall 58a of sheath extension 50 abuts inner wall 145c of tip 145. Spikes 60 are held in their extended position (FIG. 8B) by the continuous abutting contact between collar 53 and ridge 54, against the compression of spring 51. When anchor 20 has been extended to the position in FIG. 8B, the user may then hold anchor 20 and spikes 60 in this position using lock 270 of needle control 250.

When needle 20 is withdrawn, the spikes 60 are pulled back into the distal section 114 by the compression force of spring 51. Spring 51 is helical and is compressed between a rim 56 formed on the outer surface of the sheath 50 and a rim 51a that may be formed on the compression cage 146 of the catheter or its outer sheath 116-D. In addition or as an alternative to using a compression spring to draw the spikes back into the distal sheath 114, the needle 20 may have a second collar, located to the right of ridge 54 in FIGS. 8A-8B, so that the retreating needle 20 may draw the spikes back into the distal sheath section 114 by abutting contact between the distal, second collar and ridge 54. Thus, in this embodiment needle 20 deployment, as well as retraction using dial 254 may extend and retract spikes 60 as well.

As will be appreciated, embodiments of a deflection catheter using a spike anchoring mechanism may be operated according to the same steps described earlier. That is, the steps for deployment and retraction of needles 20 and 30, without a separate anchoring mechanism, may be the same as when a spike anchoring mechanism is provided at distal section 114.

A second embodiment of an anchoring mechanism is depicted in FIGS. 9A-9D. In this embodiment, an anchoring mechanism includes a helix 72 having a sharpened or piercing tip 72a that is mounted at the end 70c of a sheath extension 70. Here, the anchoring helix 72 with a piercing end 72a is engaged into the tissue by rotation about needle axis A using wheel 266 of needle control 250. The helix 72 rotates, and the needle 20 extends through a modified tip 146 having an enlarged central opening 146a.

Figure 9A:
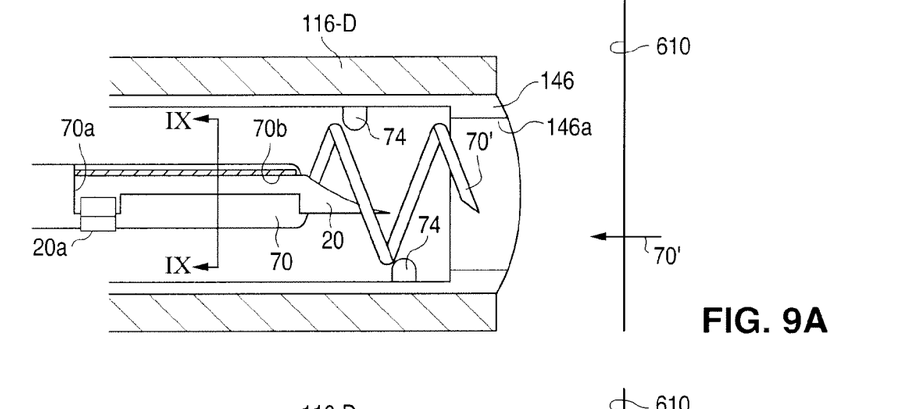
FIGS. 9A-9D are side cross-sectional views and front view, respectively, of a second embodiment of an anchor mechanism for the catheter disposed adjacent to ischemic tissue.
Figure 9B:
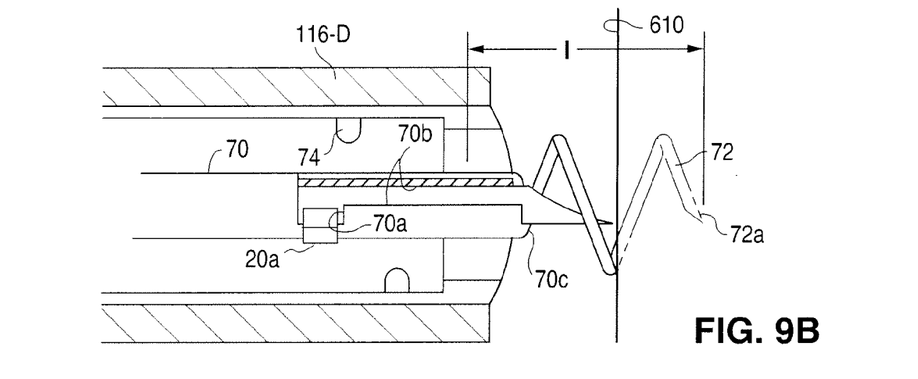
Figure 9C:
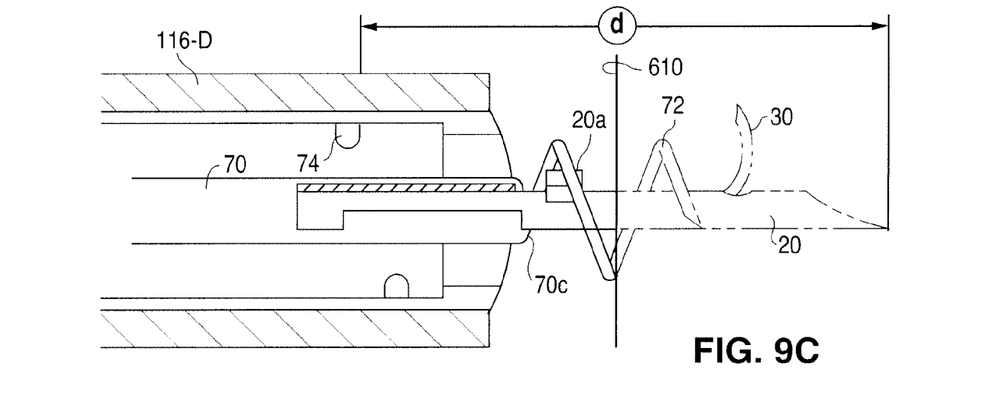

FIG. 9A depicts the position of helix 72 and needle 20 in their stowed states, that is, retracted within distal section 114 before distal section 114 has reached the target tissue 610. FIG. 8B depicts the position of helix 72 when fully deployed and embedded within the tissue 610. FIG. 9C depicts the helix 72 and needle 20 in a fully deployed state and embedded in the tissue 610. Injection needle 30 is extended to deposit therapeutic agent. With the configuration of FIG. 9C the helix 72 can prevent rotation of distal section 114 as a user 20 applies a torque to needle anchor 20 (as discussed earlier).

The rotation direction for the anchoring helix 72 when it enters the tissue should be the same as the needle 20 when rotated to re-position opening 26 at different angular stations for depositing agent into the tissue. In this way, needle rotation will tend to urge helix 72 into engagement with the tissue if there is any tendency for distal section 114 to rotate with needle 20 when a torque is applied to the needle 20 at the proximal end. Thus, for example, if looking in the direction 70' in FIG. 9A, the winding of helix 72 means that it will enter the tissue by a clockwise rotation. Turning now to FIG. 9C, needle 20, when rotated to position opening 26 towards different treatment sites, should be rotated in the clockwise direction as well. If instead needle 20 is rotated counterclockwise, then any tendency for distal section 114 to rotate with the needle 20 may cause the helix to remove itself from the tissue. However, if counterclockwise rotation of the needle is desired, the removal tendency of the helix may be overcome by applying forward pressure to increase friction between the helix and tissue, or through addition of other features such as barbs or other retention features known in the art.

In the illustrated embodiment, all aspects of the catheter 1, needle control 250 and method of use previously mentioned may be the same, except the following additional features provided by the helix, and related mechanism(s)/structure to facilitate deployment and retraction of helix 72 during a procedure. As before, needle 20 extends through the center of the sheath extension 70. At a proximal end thereof extension 70 terminates. Extension 70 may be coupled to sheath 40, or may be separate from sheath 40.

Both sheath 70 and helix 72 may be an integral unit, and anchor needle 20 may be used to deploy and retract the helix 72 when anchor needle is extended and retracted (as previously discussed in connection with spike anchor). In one embodiment, the helix 72 may be part of the same sheath 50 used for the spike anchor. That is, helix 72 deployment would be achieved by abutting a collar 53 of the needle 20 against a ring 54 formed on the inner surface of a sheath 50, which is spring biased to retract the helix 72 into the catheter distal section 114, or no spring bias may be needed (as discussed earlier). A complimentary helical guide path, e.g., guides 74 as shown in FIG. 9A, can be formed on an inner surface of sheath 116-D so that rotational motion of helix 72 is induced as the advancing needle 20 presses helix 72 forward. As before, once fully deployed the helix 72 and needle 20 may be held in place, and then released using lock 270 of needle control 250.

In the illustrated embodiment of FIGS. 9A-9D, a different mechanism is used. According to this embodiment, the helix 72 is first translated towards the right in FIG. 9A, then rotated so that it penetrates the tissue wall 610. Since the helix 72 is first translated, the guides 74 would not be necessary to induce rotation when helix 72 is pushed forward.

Figure 9D:
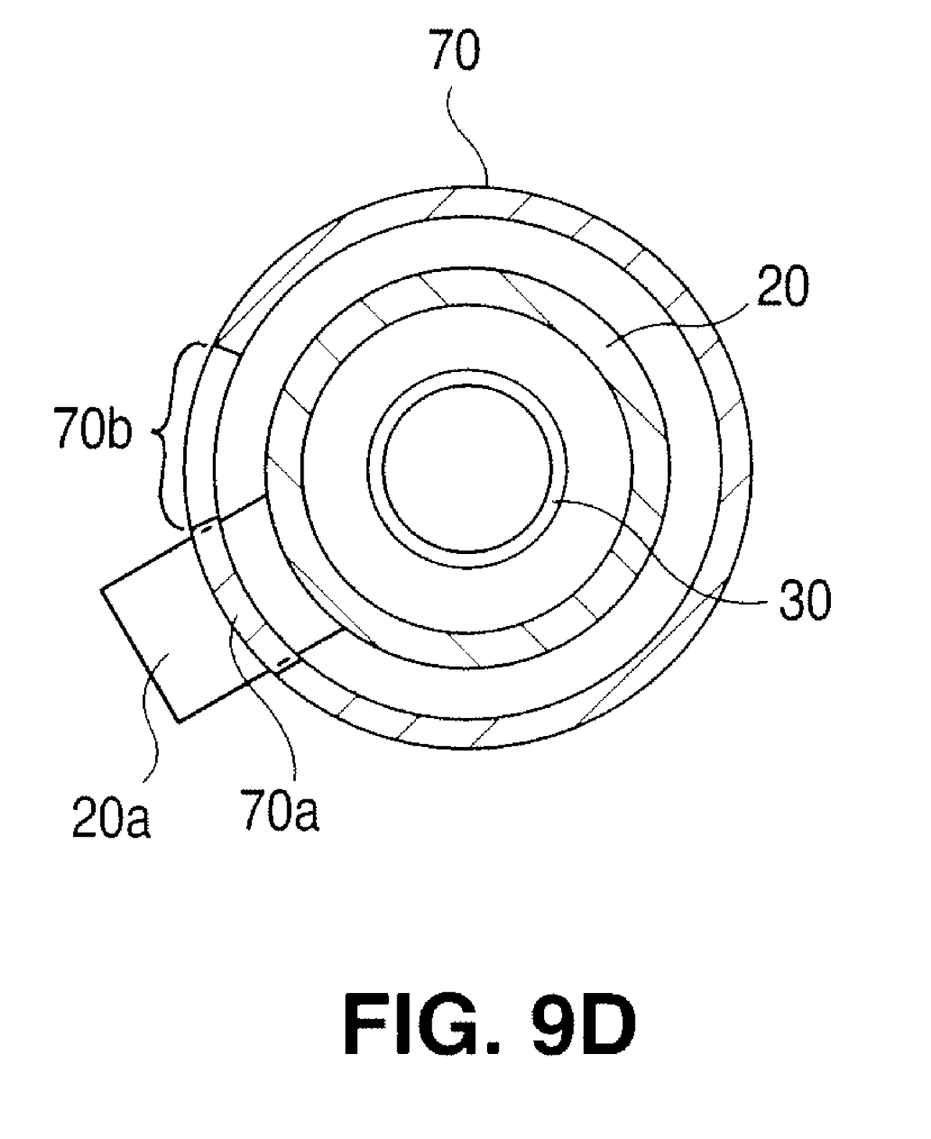

According to the illustrated embodiment, an L-shaped cutout is formed in the sheath 70. This L-shaped cutout includes a notch section 70a and a straight section 70b extending from the notch section to the distal end 70c of the sheath 70. Notch 70b and straight 70a sections are sized to receive a guide 20a formed or fixed to the outer surface of needle 20. FIG. 9D depicts a frontal view of notch section 70a and 70b and needle anchor guide 20a (section IX-IX of FIG. 9A).

When needle 20 is turned using wheel 266 and guide 20a located in notch 70a, this will cause helix 72 to rotate as well. Needle 20 may be rotated independently of helix 72 by passing guide 20a through straight section 70b using dial 254 of the needle control 250. Once guide 20a is disposed to the right of end 70c, needle 20 may be rotated independently of helix 72 so that the opening 26 of needle 20 can be moved among different angular positions for treatment of the target tissue. When the procedure is complete, the needle 20 is retracted back into straight section 70a and then rotated counterclockwise to withdraw helix 72 from the tissue.

A procedure using a helix anchor mechanism may proceed as follows. Distal tip 170 of the catheter is located at the target tissue site (FIG. 9A). Next, needle 20, with guide 20a disposed in notch 70a, is advanced forward until the tip 72a of helix 72 abuts the tissue target 610. Needle is then rotated counterclockwise using wheel 266 so that helix 72 can advance into the tissue target 610. As helix 72 advances forward, it will tend to want to pull needle 20 forward, or pull tissue 610 towards tip 146. Therefore, it may be desirable to not lock needle 20 in translation so that needle 20 can be allowed to advance forward as helix 72 is rotated into the tissue.

Once helix 72 is embedded into the tissue, needle 20 is rotated to free it from notch 70a, and then advanced along straight section 70b using dial 254. After guide 20a is free of the L-shaped section, needle 20 is locked in place using lock 270. With needle 20 now embedded within the tissue 610, it may be rotated to re-position needle 30 using dial 266 (as before). After the tissue has been treated, the lock 270 is released and needle 20 retracted back through straight section 70b of sheath 70. When located within straight section 70b, wheel 266 is rotated counterclockwise to remove helix 72 from the tissue. After helix 72 has been removed from the tissue 610, dial 254 is used to retract needle 20 and helix 72 into distal sheath 114. As an alternative embodiment, the sheath may be used for axial and rotational movement of the helix. In such case, a slot or notch may not be necessary.

A Method of Use

Figure 10:
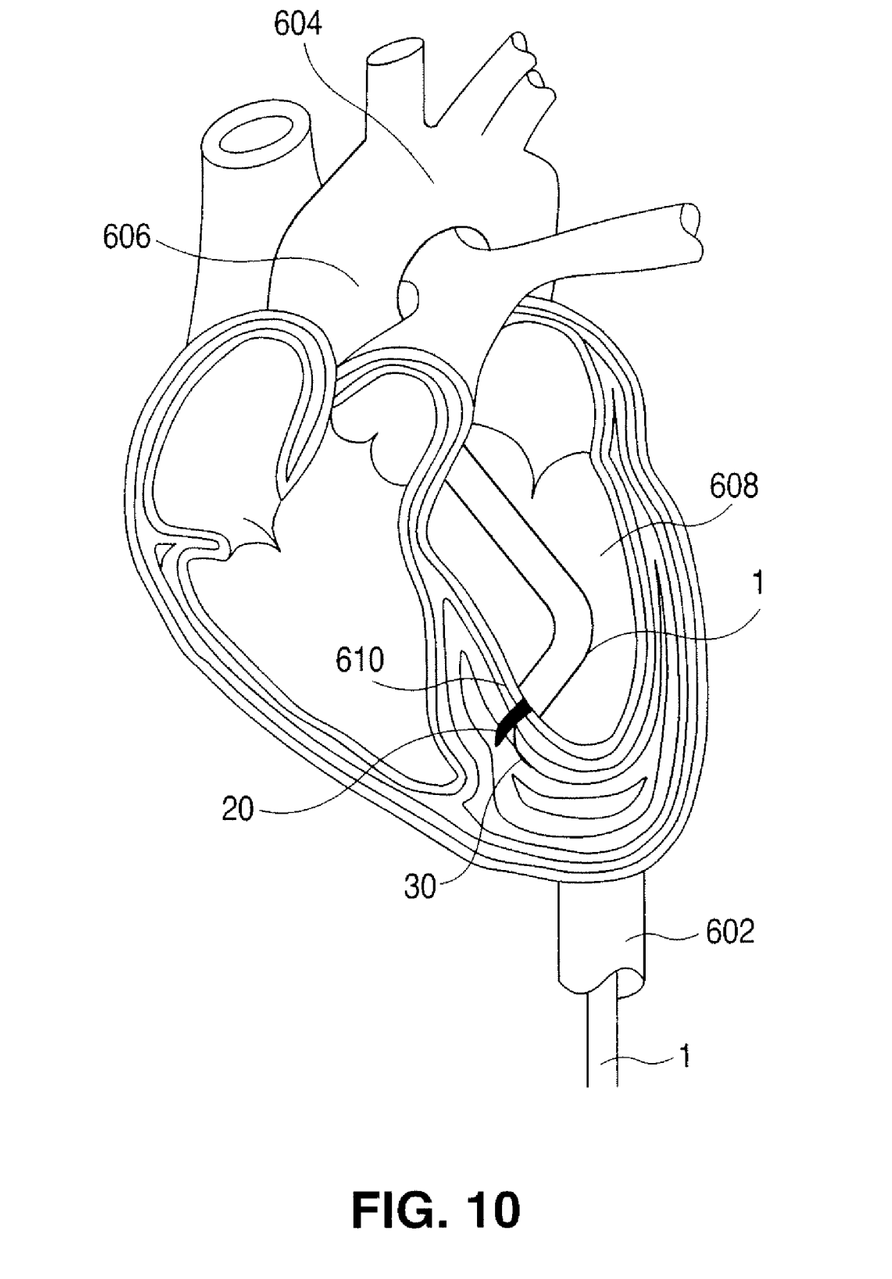
FIG. 10 is a view of the heart with the catheter located to treat ischemic tissue.

FIG. 10 illustrates the catheter 1 disposed within a patient's heart and positioned to deliver an agent into the left ventricle. The catheter 1 is inserted into the femoral artery in the groin region (not shown) through an access path created by a percutaneously placed introducer sheath as is well known in the art. The catheter 1 travels into the descending aorta artery 602, over the aortic arch 604, down the ascending aorta 606, across the aortic valve (not shown) and into the left ventricle 608.

Target injection sites (e.g., a target injection site 610) have been determined prior to the delivery procedure. The operator manipulates the catheter 1 to reach target 610 location. The manipulation is done by motions of sliding the catheter 1 up and down the ventricle 608 cavity, rotating the catheter 1 to reach different targets in the radial directions (e.g., anterior, lateral, septal wall), and deflecting the catheter distal section 114 to reach the wall. Once the catheter tip is in contact with the target wall 610, the operator extends anchor needle 20, or anchor needle 20 with helix 72 or spikes 60 into the target tissue 610, thereby anchoring the catheter at the target.

Injection needle 30 is then extended, and a prescribed dose of bio-agent injected into the tissue, the needle 30 retracted, needle 20 rotated into a new position, the needle extended towards the new location and a second dose of bio-agent injected, etc. The process may be repeated until the desired number of injections have been performed. Thus, a more uniform and repetitive pattern of injections is achieved without the need to remove and then re-insert needle 20 into the tissue. The contact of the catheter with the ventricular wall can be easily identified. The catheter tip will be seen bouncing with the wall at every contraction cycle and the EKG signal will also change. When the procedure is complete, the catheter is withdrawn from the vasculature.

The injection needle 30 of the disclosure can be used to deliver a wide range of therapeutic agent or biologic such as cells, drugs, or other fluids. For examples, biological agents such as growth factors (endothelial growth factor (VEFG) and fibroblast growth factors (FGF)), angiogenic agents (angiostatin and endostatin), cells (myogenic cells, bone marrow derived stem cells, endothelial cells, cardiomyocytes), genetic materials (DNA, RNA (virus or other vector based), and iRNA), biochemical agents, small molecule agents, and/ or any combination of the above agents, can be delivered using the needles included in the catheter assemblies previously described.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A deflection catheter for delivery of a therapeutic agent to myocardial ischemic tissue, comprising:
   a first needle including a piercing tip and a shaft defining a needle axis, the shaft forming a lumen terminating at a shaft opening located at a side of the shaft;
   a distal section of the catheter configured for being steered through a body lumen, the distal section having a catheter axis and a terminal end forming an opening for passage of the first needle;
   a second needle located within the shaft lumen and placed in fluid communication with the therapeutic agent;
   a control unit configured to extend and withdraw the second needle from the shaft opening at an angle to the needle axis while the shaft opening is embedded within the myocardium and translate and rotate the first needle relative to the distal section;
   a sheath forming a lumen for passage of the first needle, the sheath having a distal end and an opening at the distal end for passage of the first needle;
   a helical anchor coupled to the distal end of the sheath for holding the catheter distal end at the myocardium wall;
   a deployment portion of the distal section for deploying the anchor, including
      an L-shaped cutout in the sheath including a first notch portion extending parallel to the needle axis and a second notch portion extending clockwise about the needle axis, the second notch portion including a first abutting surface,
      a needle guide extending transversely from the surface of the needle shaft and forming a second abutting surface, the guide sized for being received in the first and second notches, wherein the guide is capable of being removed from the L-shaped cutout by translation and counterclockwise rotation of the first needle by actuation of the control unit;
   a first configuration of the distal section including the guide being disposed within the second notch so that when the first needle is rotated clockwise by the control unit, thereby engaging the first and second abutting surfaces, the guide is retained within the second notch while the anchor is displaced distally and rotated clockwise with the first needle; and
   a second configuration of the distal section including the guide being disposed distally of the sheath opening to enable the first needle to translate or rotate without displacing the anchor.

2. The deflection catheter of claim 1, wherein the angle is greater than 90 degrees relative to the needle axis.

3. The deflection catheter of claim 1, wherein a portion of the shaft lumen proximal the opening is sloped such that the second needle is extended and withdrawn from the shaft opening at the angle to the axis.

4. The deflection catheter of claim 1,
   wherein the second needle has a shaft portion shaped to have a curvilinear form, such that when the shaft portion is extended outwardly from the shaft opening the shaft portion takes the curvilinear form.

5. The deflection catheter of claim 4, the control unit including a second member coupled to the second needle and configured to selectively extend and withdraw the second needle distal end from the opening, such that after rotation of the shaft through one of the plurality of angles, the second needle is extendable towards an ischemic tissue target.

6. The deflection catheter of claim 4, wherein the shaft portion is shaped so that when the shaft portion extends outwardly a first distance from the shaft opening the second needle forms a first angle with respect to a needle axis, and when the shaft portion extends outwardly a second distance from the shaft opening the second needle forms a second angle with respect to the needle axis, the second angle being greater than the first angle.

7. A deflection catheter, comprising:
- a first needle including a piercing tip and a shaft defining a needle axis, the shaft forming a lumen terminating at a shaft opening located at a side of the shaft;
- a distal section of the catheter configured for being steered through a body lumen, the distal section having a catheter axis and a terminal end forming an opening for passage of the first needle;
- a second needle located within the shaft lumen and placed in fluid communication with a therapeutic agent;
- a sheath including a lumen and an opening for passage of the first needle;
- the sheath including a notch configured for selectively coupling and decoupling the first needle from the sheath;
- an anchor connected to the sheath opening; and
- a first configuration of the distal section including the first needle being coupled to the sheath via the notch, the first configuration adapted for enabling deployment of the anchor by translation of the first needle; and
- a second configuration of the distal section including the first needle being decoupled from the notch, the second configuration adapted for enabling the second needle to deliver therapeutic agent without displacing the anchor.

8. The deflection catheter of claim 7, wherein the notch is disposed at the sheath distal end.

9. The deflection catheter of claim 8, wherein the notch is an L-shaped notch.

10. The deflection catheter of claim 9, wherein the needle includes a raised surface, and wherein the first needle is coupled to the notch when the raised surface is disposed within the notch.

11. The deflection catheter of claim 7, further including a control unit including a rotation portion and translation portion for rotating and translating, respectively, the first needle, wherein the first needle and sheath are coupled and/or de-coupled from the notch by actuation of both the translation and rotation portions of the control.

12. A method for re-configuring a deflection catheter, comprising the steps of:
- providing a first needle including a piercing tip and a shaft defining a needle axis, the shaft forming a lumen terminating at a shaft opening located at a side of the shaft, a distal section of the catheter configured for being steered through a body lumen, the distal section having a catheter axis and a terminal end forming an opening for passage of the first needle, a second needle located within the shaft lumen and placed in fluid communication with a therapeutic agent, and a sheath having a distal opening and an anchor connected to the sheath;
- coupling the sheath to the first needle for enabling deployment of the anchor using the first needle; and
- decoupling the first needle from the sheath for enabling a plurality of orientations for the second needle without displacing the anchor.

13. The method of claim 12 wherein the coupling and decoupling steps further include the step of engaging and disengaging, respectively, the first needle from a notch disposed in the sheath.

14. The method of claim 12, wherein the coupling and decoupling steps further include the step of engaging and disengaging the first needle from an L-shaped notch disposed in the sheath.

15. The method of claim 12, wherein following the decoupling step a raised surface of the first needle is distal of the sheath opening.

16. The method of claim 15, wherein following the decoupling step, further including re-coupling the first needle and sheath including disposing the raised surface proximal of the sheath opening.

* * * * *